United States Patent [19]

Valerio et al.

[11] Patent Number: 5,627,210
[45] Date of Patent: May 6, 1997

[54] BRANCHED COMBINATORIAL LIBRARIES

[75] Inventors: Robert Valerio, Cranbourne South; Jian-Xin Wang, Melbourne, both of Australia

[73] Assignee: Chiron Corporation, Emervylle, Calif.

[21] Appl. No.: 385,112

[22] Filed: Feb. 6, 1995

[51] Int. Cl.$^6$ .................... A61K 31/24; A61K 31/195; A61K 31/16; C07C 233/00
[52] U.S. Cl. .................... 514/535; 514/563; 514/616; 560/24; 560/158; 562/433; 562/561; 562/564; 564/153
[58] Field of Search .................... 564/153; 562/433, 562/561, 564; 560/24, 158; 514/616, 563, 535

[56] References Cited

U.S. PATENT DOCUMENTS

| | | | |
|---|---|---|---|
| 4,237,046 | 12/1980 | Bodansky | 530/327 |
| 5,010,175 | 4/1991 | Rutter et al. | 530/334 |
| 5,124,155 | 6/1992 | Reich | 424/428 |
| 5,182,366 | 1/1993 | Heubner et al. | 530/334 |

FOREIGN PATENT DOCUMENTS

| | | |
|---|---|---|
| 91735/82 | 7/1983 | Australia. |
| 0138555B1 | 4/1989 | European Pat. Off.. |
| 86/06487 | 11/1986 | WIPO. |
| 91/19735 | 12/1991 | WIPO. |
| 92/10587 | 6/1992 | WIPO. |
| 94/06451 | 3/1994 | WIPO. |

OTHER PUBLICATIONS

Waki et al., *Synthesis* (1981) ??:266–268.
Valerio et al., *Int. J. Peptide Protein Res.* (1994) 44:158–165.

Sigma *Peptides and Amino Acids Product Catalogue* (1993–1994) pp: 111–112 and 152–153, Product No's L8901, O 3631, B 7376 and B8126.
Gross E. et al., *The Peptides* (1981) 3:203–205, 217, 241–245, 254–255 & 283 Published by Academic Press (N.Y.).
Gross E. et al., *The Peptides* (1983) 5:66–75 and 135–136 Published by Academic Press (N.Y.).

*Primary Examiner*—Joseph Conrad
*Attorney, Agent, or Firm*—Grant D. Green; Robert P. Blackburn

[57] ABSTRACT

Combinatorial libraries comprising compounds of the formula

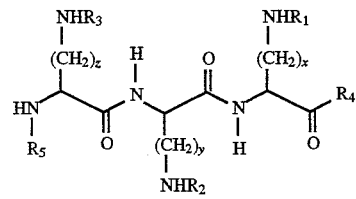

where $R_1$, $R_2$, and $R_3$ are each independently groups of the formula —C(O)R, where R is an organic radical;

x, y, and z are each independently 1, 2, 3, or 4;

$R_4$ is alkyl, alkenyl, aryl, aralkyl, acyl, amino, hydroxy, alkoxy, aryloxy, arylalkoxy, heterocyclyl, or H, or is a solid support; and $R_5$ is alkyl, alkenyl, aryl, aralkyl, acyl, amino, hydroxy, alkoxy, aryloxy, arylalkoxy, heterocyclyl, or H are disclosed.

6 Claims, No Drawings

BRANCHED COMBINATORIAL LIBRARIES

DESCRIPTION

1. Field of the Invention

This invention relates to the fields of organic chemistry and drug design. More specifically, the invention relates to the preparation of branched combinatorial compound libraries and their screening for pharmaceutical activity.

2. Background of the Invention

Geysen, EP 198855, disclosed a method for the simultaneous synthesis of a large number of different peptides. Basically, this method involves the synthesis of peptides on a solid polymeric surface, such as polyethylene, which may be molded into the shape of a rod or pin. In a preferred embodiment of the method, these rods or pins are positioned in a holder so that they form a 12 by 8 matrix, with the rods or pins being positioned so that the spacing corresponds to that of the wells of microtiter plates which are widely used for ELISA (enzyme-linked immunosorbent assay) tests.

Huebner et al., U.S. Pat. No. 5,182,366 (incorporated herein by reference) disclosed a method for preparing large mixtures of peptides on solid phase resins in equimolar ratios. This enables one to quickly search for compounds that bind to or react with a ligand by contacting the ligand (e.g., a bound receptor) with a set of peptide mixtures and noting which members of the set bind or react. Typically, the sets are prepared by specifying a known amino acid at one or two positions of an oligopeptide and providing mixtures of amino acids at the other positions. Thus, one peptide mixture might consist of a pool of hexapeptides of the formula Gly-Gly-$X_1$—$X_2$—$X_3$—$X_4$, where each X indicates that all amino acids are found at that position. The next peptide mixture would be Gly-Ala-$X_1$—$X_2$—$X_3$—$X_4$, followed by Gly-Cys-$X_1$—$X_2$—$X_3$—$X_4$, and so forth. The set consisting of all of these mixtures is termed a "library." A library is screened by testing each individual mixture and noting which mixtures produce a positive response. In some formats, the mixtures may be screened simultaneously. The positive mixtures are then resynthesized with additional positions specified. Thus, for example, if the mixture containing Phe-Tyr-$X_1$—$X_2$—$X_3$—$X_4$ was positive, the next mixture synthesized might be Phe-Tyr-Gly-$X_2$—$X_3$—$X_4$. This process (called "deconvolution") is reiterated until individual peptides are synthesized and tested.

Bartlett et al, WO91/19735, and Zuckermann et al., WO94/06451 disclosed a method for extending combinatorial library synthesis to compounds other than peptides. Bartlett and Zuckermann disclosed modular compounds based on N-substituted polyamides, poly-carbamates, and other backbones, which permits one to research non-peptide compounds.

SUMMARY OF THE INVENTION

One aspect of the invention is a compound of the formula:

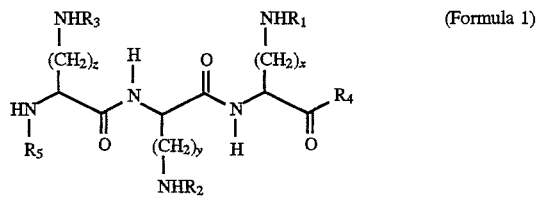

(Formula 1)

Another aspect of the invention is a combinatorial library of compounds of Formula 1.

Another aspect of the invention is a composition comprising a compound of Formula 1 and a pharmaceutically acceptable excipient.

Another aspect of the invention is a method for determining pharmaceutically active compounds by testing a combinatorial library of compounds of Formula 1.

Another aspect of the invention is a method for preparing a combinatorial library of compounds of Formula 1.

DETAILED DESCRIPTION

Definitions

The term "Compound of Formula 1" refers to compounds of the formula:

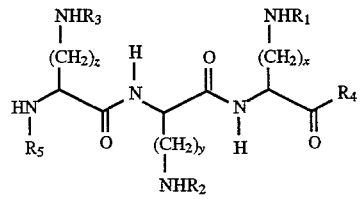

where $R_1$, $R_2$, and $R_3$ are each independently groups of the formula —C(O)R, where R is an organic radical; x, y, and z are each independently 1, 2, 3, or 4; $R_4$ is alkyl, alkenyl, aryl, aralkyl, acyl, amino, hydroxy, alkoxy, aryloxy, arylalkoxy, heterocyclyl, or H, or is a solid support; and $R_5$ is alkyl, alkenyl, aryl, aralkyl, acyl, amino, hydroxy, alkoxy, aryloxy, arylalkoxy, heterocyclyl, or H.

The term "combinatorial library" refers to a set of compounds having an oligomeric modular structure, wherein all members of the library are formed by essentially identical reactions (differing only in the reactants added), where the diversity of the library results from the combination of a variety of monomers in several positions within the molecule. For example, a combinatorial peptide library might consist of the peptides Ala-Gly-Cys, Ala-Gly-Gly, Ala-Gly-Ala, Ala-Ala-Ala, Ala-Cys-Ala, Ala-Cys-Gly, Gly-Ala-Ala, Gly-Ala-Cys, and so forth. Combinatorial libraries of the present invention may achieve a much greater degree of diversity due to the ready availability of compounds (particularly carboxylic acids) which may be easily coupled in positions $R_1$, $R_2$, and $R_3$. A combinatorial library may include mixtures of compounds, or may consist entirely of individual compounds.

The term "mixture" as used herein refers to an aliquot of compounds, either in solution or bound to a particulate solid phase, which may be assayed simultaneously.

The term "organic radical" refers to a carbon-containing moiety having a molecular weight of less than 300 g/mol. Organic radicals within the scope of the invention include, without limitation, alkyl (for example, methyl, butyl, dodecyl), cycloalkyl (for example, cyclohexyl, cyclopentyl), alkenyl, alkynyl, aryl (for example phenyl, naphthyl), aralkyl (for example, benzyl, naphthylmethyl), aryl-alkenyl, aryl-alkynyl, alkoxy, alkenyloxy, alkynyloxy, aryloxy, aralkyloxy, aryl-alkenyloxy, alkynyloxy, alkylamino, dialkylamino, arylamino, N-alkyl-N-arylamino, alkylthio, arylalkylthio, alkylsulfinyl, alkylsulfonyl, acyl, aryl-acyl, aralkyl-acyl, acyloxy, acylamino, acylthio, carbamoyl, thiocarbamoyl, heterocycloalkyl with or without unsaturation (for example 2-furyl, tetrahydrofuryl, piperidyl), heteroaryl (for example, pyridyl, quinolinyl), and the like, where any of these may be substituted with 1-6 substituents such as halo, alkyl, haloalkyl, nitro, amino, hydroxy, alkylamino, dialkylamino, thio, acyl, alkoxy, acyloxy, and the like.

The term "alkyl" as used herein refers to saturated hydrocarbon radicals containing from 1 to 30 carbon atoms, inclusive. Alkyl radicals may be straight, branched, or cyclic. Exemplary alkyl radicals include n-pentyl, n-hexyl, n-octyl, n-dodecyl, 2-dodecyl, 4-octadecyl, 3,5-diethylcyclohexyl, duryl, and the like. The term "lower alkyl" as used herein refers to straight, branched, and cyclic chain hydrocarbon radicals having from 1 to 8 carbon atoms, such as methyl, ethyl, propyl, isopropyl, n-butyl, s-butyl, t-butyl, n-pentyl, n-hexyl, cyclopentyl, cyclohexyl, 2-methylcyclopentyl, cyclopentylacetyl, and the like. "Alkoxy" refers to radicals of the formula ;—OR, where R is alkyl as defined above: "lower alkoxy" refers to alkoxy radicals wherein R is lower alkyl. "Hydroxy-lower alkyl" refers to radicals of the formula HO—R—, where R is lower alkylene of 1 to 8 carbons, and may be straight, branched, or cyclic. "Hydroxy-lower alkoxy" refers to radicals of the formula HO—R—O—, where R is lower alkylene of 1 to 8 carbons, and may be straight, branched, or cyclic. "Lower alkoxy-lower alkyl" refers to groups of the formula $R_aO$—$R_b$—, where $R_a$ and $R_b$ are each independently lower alkyl. "Lower alkoxy-lower alkoxy" refers to groups of the formula $R_aO$—$R_bO$—, where $R_a$ and $R_b$ are each independently lower alkyl.

"Alkenyl" refers to hydrocarbon radicals of 2–20 carbon atoms having one or more double bonds. Alkenyl radicals may be straight, branched, or cyclic. Exemplary alkenyl radicals include 1-pentenyl, 3-hexenyl, 1,4-octadienyl, 3,5-diethylcyclohexenyl, and the like. "Lower alkenyl" refers to alkenyl radicals having 2–8 carbon atoms.

The term "alkynyl" refers to hydrocarbon radicals of 2–20 carbon atoms having one or more triple bonds. Alkynyl radicals may be straight, branched, or cyclic. Exemplary alkynyl radicals include 1-pentynyl, 3-hexynyl, octa-2-yn-6-enyl, 3,5-diethylcyclohexynyl, and the like. "Lower alkynyl" refers to alkynyl radicals having 2–8 carbon atoms.

The term "cycloalkyl" refers to alkyl radicals of 3–20 carbon atoms having at least one ring of carbon atoms. "Bicycloalkyl" refers to alkyl radicals of 7–20 carbon atoms having at least two fused rings of carbon atoms (in which one or more carbon atoms are members of both rings). "Tricycloalkyl" refers to alkyl radicals of 7–20 carbon atoms having at least three fused rings of carbon atoms (in which one or more carbon atoms of each ring are simultaneously members of another ring).

The term "haloalkyl" refers to an alkyl radical substituted with one or more halogen atoms. Exemplary haloalkyl radicals include trifluoromethyl, 2,2,2-trifluoroethyl, 3-chlorocyclohexyl, 2-bromo-3-chlorocyclohexyl, 2,3-dibromobutyl, and the like.

The term "haloalkenyl" refers to an alkenyl radical substituted with one or more halogen atoms. Exemplary haloalkenyl radicals include 3-chloroprop-2-enyl, 4,4-dichlorobut-2-enyl, 5-bromo-3-methylcyclohex-2-enyl, and the like.

"Aryl" refers to aromatic hydrocarbons having up to 14 carbon atoms, preferably phenyl or naphthyl. "Aryl-lower alkyl" refers to radicals of the form Ar—R—, where Ar is aryl and R is lower alkyl. "Aryloxy" refers to radicals of the form Ar—O—, where Ar is aryl. "Aryloxy-lower alkyl" refers to radicals of the form ArO—R—, where Ar is aryl and R is lower alkyl.

The term "acyl" refers to a radical of the formula RCO—, in which R is H, alkyl as defined above, phenyl, benzyl or naphthyl. Exemplary acyl groups include acetyl, propionyl, formyl, t-butoxycarbonyl, benzoyl, and the like. "Lower acyl" refers to radicals wherein R is lower alkyl.

The term "halo" refers to a halogen radical, such as F, Cl Br, or I.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of opiate addiction in a patient may be reduction of opiate effect (blockade), or the prevention of relapse in a patient who has been cured.

The term "uPA-mediated disorder" refers to a disease state or malady which is caused or exacerbated by a biological activity of uPA. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF is also mitogenic for some tumor cells (e.g., SaOS-2 osteosarcoma cells), which sometimes self-activate in an autocrine mechanism. Accordingly, the huPAR antagonist of the invention is effective in inhibiting the proliferation of uPA-activated tumor cells.

The term "effective amount" refers to an amount of huPAR antagonist compound sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

General Methods and Detailed Description

The libraries of the invention may be prepared either on solid-phase supports (e.g., on resins suitable for peptide synthesis, Multipin system crowns, and the like), or may be prepared in solution. It is presently preferred to synthesize libraries on solid phase supports due to the ease in handling that results. In general, the libraries may be synthesized and assayed in situ (bound to the solid phase), or may be cleaved from the support and assayed in solution. In situ assay is sometimes advantageous, as where the library is provided as a spatially addressable array of compounds (where the identity of an active compound is determined by its position within the array): see, for example, EP 138555 B1, and WO92/10587, both incorporated herein by reference. However, assay in solution is presently preferred, as solution phase is most like the expected environment in which the compound will be active.

Oligomers of the invention are preferably assembled in a "submonomer" fashion (where the backbone segment and the sidechain constitute a "monomer" despite being added to the oligomer separately), with a backbone segment added to the support, the sidechain site deprotected, the sidechain added, the backbone site deprotected, the next backbone segment added, and so forth until the desired size of oligomer is obtained. In general one may prepare oligomers of the invention having from two to about twenty monomers, however, presently preferred oligomers have about two to about five monomers, preferably about three monomers.

Where the oligomers are synthesized as libraries, one may employ either the "split resin" method or the "mixed reactant" method. In the "split resin" method, mixtures are formed by dividing the support into a number of aliquots equal to the number of different monomers to be added, adding a different monomer to each aliquot, and recombining the aliquots to form a mixture. The "split resin" technique allows one to drive each reaction to completion by using an excess of reactants, without concern over differing reaction rates (see, for example, U.S. Pat. No. 5,182,366, incorporated herein by reference). However, it limits one to no more than one compound per support particle (all compounds attached to a particular support will necessarily be identical). This is not a significant limitation if the number of support particles is large compared to the number of compounds in the library (for example, where one uses finely divided support resin to synthesize a library of $10^4$–$10^5$ compounds). In the "mixed reactant" method, a mixture of monomers is added simultaneously. If the different monomers couple at different rates, one may adjust the concentrations of the monomer reactants in inverse, proportion to their reaction rates in order to obtain an equimolar mixture of products (see, for example, U.S. Pat. No. 5,010,175, incorporated herein by reference). One may also use hybrid methods: for example, it may be desirable to divide a pool of resin into several aliquots, and to couple a mixture of only a few similar reactants to each pool.

Oligomers may also be prepared by other methods. For example, one may completely synthesize the backbone of the oligomers first, followed by deprotection of the side, chain sites and addition of the sidechains. The side chain sites may be protected with a series of mutually orthogonal protecting groups, permitting one to remove one group at a time. Alternatively, one may add mixtures of side chain groups simultaneously.

Libraries are analyzed in a number of ways. "Deconvolution" requires that one retain information regarding one or more positions within the oligomer, while letting the other positions vary (e.g., randomly). For example, one may prepare a set of trimers in which the first one or two positions are known for each aliquot, while the third position contains a mixture of different monomers (for example, by preparing a set of pins, each pin having a different dimer, and coupling a mixture of monomers at the third position). The entire set is assayed simultaneously, and aliquots which demonstrate activity are identified. The active aliquots or pools are then resynthesized as individual compounds and tested again to determine which individual compounds are active. Alternatively, one may prepare all of the compounds individually in a spatially-addressable array, and identify the active compounds by their position within the array. Or, one may select active compounds by affinity, identifying the active compounds by chromatographic or mass spectroscopic techniques.

Compounds of the invention are administered orally, topically, or by parenteral means, including subcutaneous and intramuscular injection, implantation of sustained release depots, intravenous injection, intranasal administration, and the like. When used to treat tumors, it may be advantageous to apply the compound directly to the site, e.g., during surgery to remove the bulk of the tumor. Accordingly, compounds of the invention antagonist may be administered as a pharmaceutical composition comprising the compound in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbicare® (Allergan), Neodecadron® (Merck, Sharp & Dohme), Lacrilube®, and the like, or may employ topical preparations such as that described in U.S. Pat. No. 5,124, 155, incorporated herein by reference. Further, one may provide a compound of the invention in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of compound required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.01 mg/Kg to about 50 mg/Kg huPAR antagonist administered i.v. or subcutaneously is effective for inhibiting tissue damage due to chronic inflammation. For treating corneal angiogenesis, huPAR antagonist may be administered locally in a gel or matrix at a concentration of about 0.001 mg/Kg to about 5 mg/Kg.

EXAMPLES

The examples presented below are provided as a further guide to the practitioner of ordinary skill in the art, and are not to be construed as limiting the invention in any way.

Example 1

(Preparation of Dpr Oligomers)

Optically pure N-α-Fmoc-N-β-Alloc-D-2,3-diaminopropionic acid ("Fmoc-D-Dpr(Alloc)-OH") was prepared from Boc-D-Asparagine following published procedures. Boc-D-Dpr-OH was prepared as described by M. Waki et al., *Synthesis* (1981) 266–68, and converted to Boc-D-Dpr(Alloc)-OH (2) by reaction with allyl chloroformate in sodium carbonate/water/acetone. The product 2 was obtained as a white foam in 77% yield (mp 48°–50° C). The molecular weight was confirmed by ionspray MS (Perkin-Elmer Sciex, API III) and purity by thin-layer chromatography ($CHCl_3$/MeOH/HOAc 90:8:2) ($R_f$=0.25, one spot).

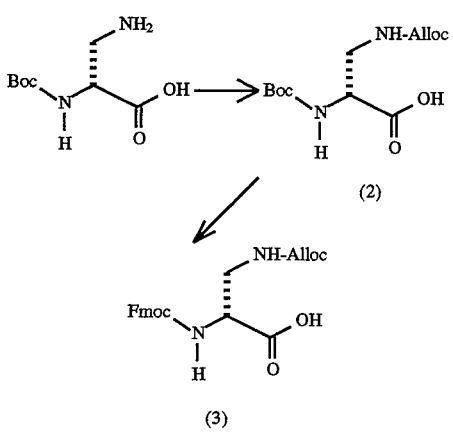

The Boc group was removed by treating 2 with 95% trifluoroacetic acid/water for 30 minutes, followed by reaction with Fmoc-OSu in sodium carbonate/water acetone to provide Fmoc-D-Dpr(Alloc)-OH (3) in 80% yield as a white foam (mp=44°–46° C.). Molecular weight was confirmed by ionspray MS, and purity by tlc as above ($R_f$ 0.50, one spot).

Ten trimers having the general structure H-[Dpr(RCO)]$_3$-NH$_2$ were prepared using Multipin solid phase synthesis (see, e.g., R. M. Valerio et al., *Int J Peptide Protein Res* (1994) 44:158–65). Crowns (support surfaces, Chiron Mimotopes Peptide Systems, Melbourne, Australia) functionalized with the TFA labile amide forming linker p-[(R,S)-α-[1-(9H-Fluoreny-9-yl)-methoxyformamido]-2, 4-dimethoxybenzyl]-phenoxyacetic acid (loading 1.2 μmole/crown) were used for synthesis. The crowns were treated with 20% piperidine/DMF (20 minutes) to remove the Fmoc group, and washed with DMF (5×2 min). Fmoc-D-Dpr(Alloc)-OH was coupled to the crowns by activation with BOP/HOBt/NMM at a concentration of 0.1M in DMF (2 hr); in situ monitoring with bromphenol blue indicated coupling was complete within 2 hr. The Alloc group was removed by treating the crowns with a solution (0.5 mL/crown) of tetrakis(triphenylphosphine) palladium (0) (0.0125M) in dry CH$_2$Cl$_2$ containing tri-n-butyltin hydride (0.24M) and acetic acid (0.315M) for 1 hr. The crowns were washed with CH$_2$Cl$_2$, DMF, 0.5% DIEA/0.5% sodium diethyldithiocarbamic acid in DMR (2×10 min) and DMF (3×2 min).

The carboxylic acid (RCOOH) was then coupled to the β-amino group of Dpr using DIC/HOBt activation at 0.15M in DMF (overnight coupling). Benzoic acid was coupled in the first position (closest the crown), with 2-naphthoxyacetic acid in the second position. In the third position, acetic acid, p-tolylacetic acid, benzoic acid, 6-hydroxynicotinic acid, Boc-4-aminobenzoic acid, cyclohexylacetic acid, 2-pyrazinecarboxylic acid, isobutryic acid, nicotinic acid, and Boc-β-alanine were coupled to individual crowns. The crowns were washed with DMF (3×2 min) between each coupling step. After coupling the first carboxylic acid, the terminal Fmoc group was removed, and the second Fmoc-D-Dpr(Alloc)-OH was coupled, followed by removal of Alloc and coupling of the second carboxylic acid. This step was repeated for the third Fmoc-D-Dpr(Alloc)-OH and third carboxylic acid.

Dpr trimers were cleaved from the crowns by treatment with 95% TFA/4% H$_2$O/1% ethanedithiol (0.25 mL/crown) for 2 hr at room temperature. The solvent was removed under a stream of nitrogen, and the residue solubilized in 60% acetonitrile/water (0.5 mL/crown). The trimers were analyzed by ionspray MS and reverse phase HPLC. All compounds gave the correct molecular ion after MS analysis. HPLC was performed on a 4 μm Merck Lichrosphere 4×250 mm C18 column, using a linear gradient from 0.1% TFA/water to 60% acetonitrile/0.1% TFA/water over 15 minutes.

Example 2

(Preparation of Library)

Proceeding as described in Example 1 above, a library of compounds was prepared consisting of 225 pools of 15 compounds per pool. In this library, the first two positions were defined (known), while the third position was synthesized as a mixture of the following carboxylic acids: acetic acid, p-tolylacetic acid, n-butyric acid, benzoic acid, picolinic acid, 6-hydroxynicotinic acid, 5-oxo-2-hydrocarboxy-tetrahydrofuran, 2-naphthoic acid, 2,5-dihydroxyphenylacetic acid, OH-methylphenoxyacetic acid, Boc-glycine, Boc-β-alanine, propionic acid, Boc-4-aminobenzoic acid, cyclohexylacetic acid, 2-pyrazinecarboxylic acid, 2-naphthoxyacetic acid, isobutyric acid, 4-hydroxybutyric acid, 4-hydroxybenzoic acid, nicotinic acid, and hydroxymethylbenzoic acid.

Example 3

(Library Screening)

The library prepared in Example 2 was screened for ability to bind to soluble human urokinase plasminogen activator (shuPA) to its receptor (huPAR) using ELISA (see US94/28145, incorporated herein by reference).

The compounds were tested at a concentration of 300 nM/pool. The pool containing XRB (mixture in the third position, 2-naphthoxyacetic acid in the second position, and p-tolylacetic acid in the first position) demonstrated sufficient activity to warrant deconvolution. The members of the XRB pool were resynthesized as individual compounds and assayed again at individual concentrations of 2 μM. The compound (4) having 4-hydroxybutyric acid in the third position demonstrated the highest affinity for huPAR (~2–5 μM affinity).

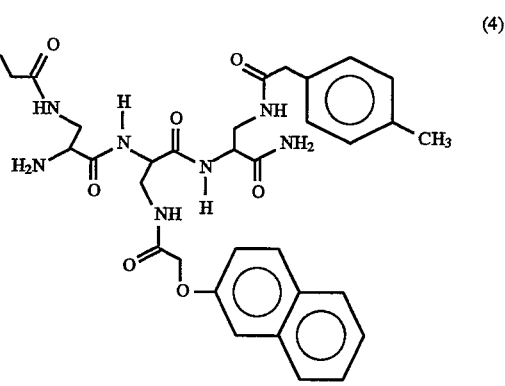

This compound (huPAR antagonist) is active in treating huPAR-mediated disorders in mammals.

What is claimed:

1. A compound of the formula:

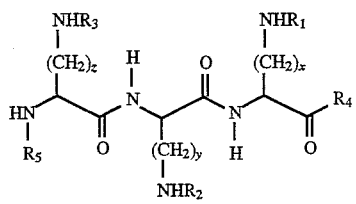

where $R_1$, $R_2$, and $R_3$ are each independently groups of the formula —C(O)R, where R is an organic radical;

x, y, and z are each independently 1, 2, 3, or 4;

$R_4$ and $R_5$ are each independently alkyl, alkenyl, aryl, aralkyl, acyl, amino, hydroxy, alkoxy, aryloxy, aryl-alkoxy, heterocyclyl, or H.

2. The compound of claim 1, wherein each R is independently alkyl, alkenyl, aryl, aralkyl, acyl, amino, hydroxy, alkoxy, aryloxy, aryl-alkoxy, or heterocyclyl; or alkyl, alkenyl, aryl, aralkyl, acyl, amino, hydroxy, alkoxy, aryloxy, aryl-alkoxy, or heterocyclyl substituted with 1–4 substituents selected from the group consisting of lower alkyl, halo, hydroxy, amino, thio, lower alkoxy, lower alkylthio, lower alkylamino, nitro, phenoxy, and benzyloxy; or H.

3. The compound of claim 2, wherein x, y, and z are each 1.

4. The compound of claim 3, wherein $R_4$ and $R_5$ are each —$NH_2$.

5. A compound of the formula

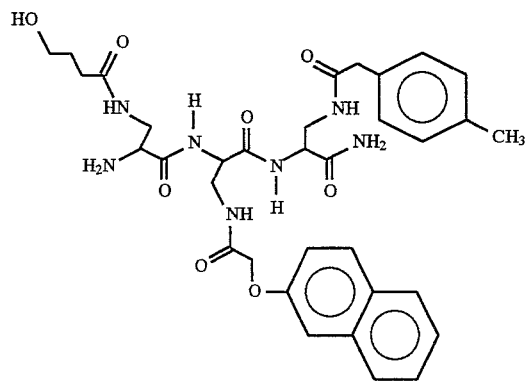

and pharmaceutically acceptable salts thereof.

6. A composition for treating a uPA-mediated disorder, said composition comprising: a compound of the formula

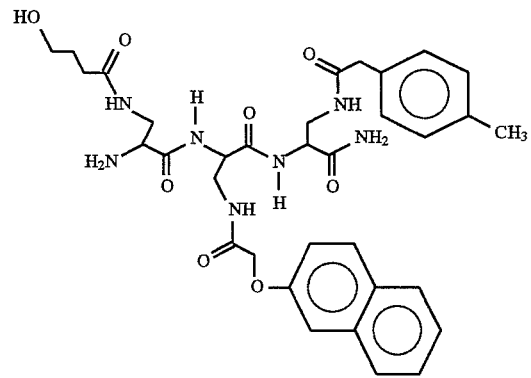

or a pharmaceutically acceptable salt thereof; and a pharmaceutically acceptable excipient.

* * * * *